United States Patent [19]

McSpadden

[11] Patent Number: 4,904,185
[45] Date of Patent: Feb. 27, 1990

[54] DENTAL INSTRUMENT
[76] Inventor: John T. McSpadden, 6918 Shallowford Rd., Chattanooga, Tenn. 37421
[21] Appl. No.: 267,032
[22] Filed: Jan. 10, 1948
[51] Int. Cl.⁴ .................................................. A61C 3/08
[52] U.S. Cl. .................................... 433/164; 433/81; 433/102
[58] Field of Search ................... 433/81, 102, 164, 224

[56] References Cited
U.S. PATENT DOCUMENTS

| 498,554 | 5/1893 | Johanson | 433/102 |
|---|---|---|---|
| 1,307,446 | 6/1919 | Kerr | 433/102 |
| 1,694,857 | 12/1928 | Kulik | 433/81 |
| 4,538,989 | 9/1985 | Apairo, Jr. et al. | 433/102 |

FOREIGN PATENT DOCUMENTS

| 279144 | 10/1913 | Fed. Rep. of Germany | 433/102 |
|---|---|---|---|
| 365050 | 12/1922 | Fed. Rep. of Germany | 433/102 |
| 2724516 | 4/1978 | Fed. Rep. of Germany | 433/81 |
| 775073 | 12/1934 | France | 433/102 |

Primary Examiner—John J. Wilson
Attorney, Agent, or Firm—Luedeka, Hodges & Neely

[57] ABSTRACT

In one embodiment, a condenser instrument for thermomechanically condensing a thermoplastic material, such as gutta percha, in the extirpated root canal of a tooth through rotation of the instrument is disclosed. The condenser instrument includes a shank having a tapered working portion along part of its length. The working portion includes a single, continuous helical flute defining a continuously helical shoulder having a negative rake angle. The shoulder is generally directed downwardly toward the tip end of the shank. A wide land is formed at the periphery of the shoulder. In a second embodiment, a remover instrument for removing a thermoplastic material, such as gutta percha, from a previously obturated root canal of a tooth through rotation of the remover instrument is disclosed. The remover instrument includes a shank having a tapered working portion along part of its length. The working portion includes a single, continuous helical flute defining a continuous helical shoulder having a negative rake angle. The shoulder is generally directed upwardly away from the tip of the shank. A wide land is formed at the periphery of the shoulder.

6 Claims, 1 Drawing Sheet

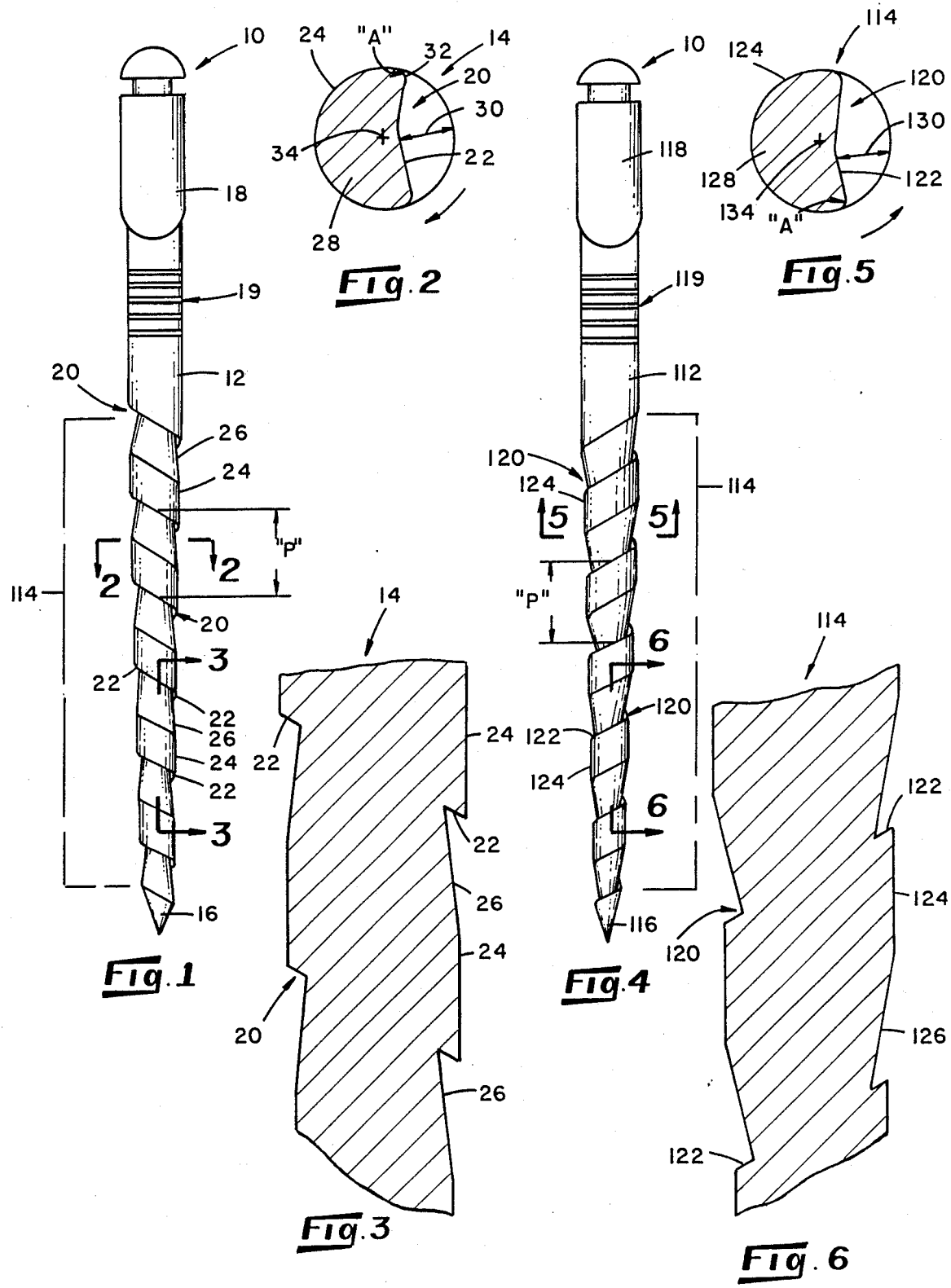

DENTAL INSTRUMENT

The present invention relates to the field of dentistry, and more particularly to the specialized field of endodontics. Specifically, in one embodiment the invention relates to a condenser instrument for thermomechanically obturating an extirpated tooth root canal with a thermoplastic material, and in another embodiment to a remover instrument for thermomechanically removing a thermoplastic material froma previously obturated root canal.

One of the more technically difficult and delicate procedures in the field of dentistry is that of obturating (filling) a extirpated (stripped) tooth root canal. The extirpated tooth root canal must be filled in a homogeneous three-dimensional manner without voids in order to prevent any leakage or communication between the root canal and the surrounding and supporting tissues of the tooth. The difficulty is further compounded by the threat of breakage of the compactor instrument and concern of extrusion of the thermoplastic material through the apical foramen of the tooth root.

Another difficult technique or process is that of removing the set thermoplastic filling material from a previously obturated tooth root canal without exerting forces on the filling material which could cause the removal instrument to break and/or cause the extrusion of the filling material through the apical foramen of the tooth.

In the typical or traditional method for obturating a tooth root canal, strand-like pieces of a thermoplastic material, conventionally gutta percha, in the form known as points or cones, is inserted into the extirpated root canal. These gutta percha points are physically compacted (condensed) by small instruments known as "pluggers" or "spreaders". It is known to employ "spreaders" and "pluggers" which are heated to soften the gutta percha points within the root canal and then manually manipulated to compact the softened gutta percha points. This procedure requires a high degree of skill on the part of the endodontist because it is necessary to condense or compact the gutta percha both vertically and horizontally. However, the process is time consuming and, unless the endodontist is highly skilled, the results are not always satisfactory.

Another method which is employed involves heating the gutta percha before it is inserted into the canal and then injecting it into the canal while it is in the plastic state. The injected gutta percha is then manually condensed with suitable instruments.

Still another method is that described in U.S. Pat. Nos. 4,353,698 and 4,457,710. In this method a mechanically driven, multi-fluted, rotatable instrument having downwardly facing helical shoulders is rapidly rotated to chop up the gutta percha points and to soften them. The helical shoulders force the plasticized gutta percha vertically towards the apical foramen. While this method secures good results, there is always a concern that high speed rotation of the instrument will damage the canal walls, that the instrument will break due to the forces involved, or that the vertical forces may cause the gutta percha to be extruded through the apical foramen.

An object of the present invention is to reduce the operating speed of a mechanically driven instrument while still providing sufficient frictionally generated heat to plasticize the gutta percha points and to balance the forces on the plasticized gutta percha to provide sufficient pressure both vertically and laterally to fill the canal while minimizing forces which might effect extrusion through the apical foramen.

Another object of the invention is to provide a condensing instrument which is easier for the endodontist to manipulate in the root canal with confidence.

It is still another object of the present invention to provide a mechanically driven remover instrument for removing set gutta percha from a previously obturated root canal.

In one embodiment, the invention provides, in a broad sense, a condensing instrument for thermomechanically obturating a root canal with a thermoplastic material, such as gutta percha, the condenser having a tapered shank with a working portion including a single continuous helical flute defining a single continuous helical shoulder. A land is formed at the periphery of the shoulder which has a width measuring at least 40 percent of the pitch of the flute.

In another embodiment, the invention provides, in a broad sense, a remover instrument for thermomechanically removing set thermoplastic material, such as gutta percha, from a previously obturated root canal, the remover instrument having a tapered shank with a working portion including a single continuous helical flute defining a single continuous helical shoulder. A land is formed at the periphery of the shoulder which has a width measuring at least 40 percent of the pitch of the flute.

These objects and advantages of the invention will become more clear upon reference to the following description and accompanying drawings in which like numerals refer to like parts and wherein:

FIG. 1 is an elevational view of an embodiment of a dental instrument embodying various features of the present invention;

FIG. 2 is an enlarged transverse cross-sectional view as seen in the direction of arrows 2—2 in FIG. 1;

FIG. 3 is an enlarged sectional view as seen in the direction of arrows 3—3 in FIG. 1;

FIG. 4 is an elevational view of another embodiment of a dental instrument embodying various features of the present invention;

FIG. 5 is an enlarged transverse cross-sectional view as seen in the direction of arrows 5—5 in FIG. 4; and, FIG. 6 is an enlarged sectional view as seen in the direction of arrows 6—6 in FIG. 4.

WIth reference to FIGS. 1 through 3, there is shown a condenser instrument, generally denoted as the numeral 10, of the present invention, which is particularly adapted for thermomechanically condensing a thermoplastic material, such as gutta percha, in the extirpated root canal of a tooth through rotative motion of the instrument 10. The condenser instrument 10 has a shank 12 with a working portion 14. The working portion 14 is tapered along its length toward a tip end 16 which may be blunt. The shank 12 above the working portion 14 is illustrated as being substantially cylindrical and is provided with a fitting 18 which is adapted to mate with the chuck of a dental hand piece (not shown). In addition, the shank 12 may be provided with indicia which can be aligned with the upper tooth structure to provide an indication of the depth of penetration of the instrument. As illustrated, these indicia are in the form of spaced rings 19 formed in the shank 12.

A single continuous helical flute 20 is formed in the tapered working portion 14 of the shank defining a helical shoulder 22. The shoulder 22 is generally directed downwardly away from the centerline of the shank 12 and toward the tip end 16 of the shank 12. As illustrated, the helical flute 22 follows a left-handed twist so that when it is rotated in a right-handed direction by the hand piece, the shoulder 22 forces the material outwardly in a generally radial direction of the working portion 14 from the centerline of the instrument 10 and downwardly toward the tip end 16 of the compactor instrument 10. However, it is contemplated that the flute 20 can follow a right-handed twist if the instrument 10 is to be operated by a hand piece which rotates it in the opposite direction.

In order to minimize abrasion with the walls of the root canal cavity, as well as generate sufficient friction to fluidize or plasticize the gutta percha, the periphery of the outer diameter of the shoulder 22 of the flute 20 is provided with a flat surface or peripheral land 24. The land 24 provides a spiraled or helical flat surface at the periphery of the working portion 14 rather than a sharp edge which may contact the walls of the root canal cavity. The diameter of the land 24 is progressively reduced as shown best in FIG. 1 to provide the tapered working portion 14.

As can be best seen in FIGS. 1 and 2, the flute wall 26 of the flute 20 tapers inwardly from the upper end of the land 24 toward the inside diameter of the next adjacent preceding shoulder 22 in a direction away from the tip end 16. The pitch of the flute 20, denoted by the letter "P", remains constant over the length of the working portion 14. The width of the peripheral lands 24, measured along the longitudinal axis of the working portion 14 is at least 40 percent of the flute pitch "P". Preferably, the width of the land 24 is 50 percent of the flute pitch "P". In addition, the width of the land 24 remains constant over the length of the working portion 14.

The helical shoulder 22 is of a constant depth along the entire length of the working portion 14 of the shank 12 and forms a web 28 which has a continuous radial web clearance 30 from the periphery of the working portion 14 as can be best seen in FIG. 2. In transverse cross-section of the shank 12, the peripheral side of the web 28 providing the land 24 measures at least 40 percent of the circumference of the working portion 14 of the shank 12. The helical shoulder 22 is generally cupped or concave, and the leading edge 32 of the shoulder 22 intersects the land 24 at the periphery of the working portion 14 at an included angle "A" of greater than 90 degrees, thus providing a negative rake angle flute. In addition, the concave shoulder 22 is asymmetrical with respect to the centerline 34 of the shank 12 so that the apex of the concavity of the shoulder 22 is offset from the shank centerline 34 toward the intersection of the shoulder 22 and land 24, i.e., toward the leading edge 32 of the shoulder 22. This configuration functions to efficiently push the plasticized gutta percha outwardly away from the shank 12.

The tooth root canal is extirpated, cleaned and shaped to provide adequate access, and gutta percha points are then inserted into the root canal in the usual manner.

The condenser instrument 10, of a size to conform with the size of the cavity is selected and coupled to the chuck of a low speed dental hand piece. The working portion 14 of the shank 12 is inserted into the tooth root canal into contact with the gutta percha. The rotation of the instrument causes the helical shoulder 22 and land 24 to generate functional heat which plasticizes the gutta percha and mechanical work the plasticized gutta percha generally radially outwardly of the shank 12 and somewhat downwardly toward the tip end 16 of the shank 12. Because of the large land 24 and the friction it provides, the instrument 10 may be rotated at speeds of from about 2000 to about 3000 R.P.M. to generate sufficient functional heat to plasticize the gutta percha. This is substantially slower that the operational speeds of heretofore known mechanically driven compactor instruments. Moreover, because of the negative rake angle, and the large land area, the gutta percha is "smeared" and softened rather than being chopped and softened. This provides a balance between lateral and longitudinal forces.

The specifications for typical instruments of various sizes are shown in the following table:

| Size | Nominal Diameter Across Shoulders at Tip mm | Working Portion Length mm | Number of Shoulders /Side/ 16 mm |
|---|---|---|---|
| 25 | 0.25 | 16.0 | 12 ± 2 |
| 30 | 0.30 | 16.0 | 10 ± 2 |
| 35 | 0.35 | 16.0 | 10 ± 2 |
| 40 | 0.40 | 16.0 | 10 ± 2 |
| 45 | 0.45 | 16.0 | 9 ± 2 |
| 50 | 0.50 | 16.0 | 9 ± 2 |
| 60 | 0.60 | 16.0 | 8 ± 2 |
| 70 | 0.70 | 16.0 | 8 ± 2 |
| 80 | 0.80 | 16.0 | 8 ± 2 |
| 90 | 0.90 | 16.0 | 5 ± 2 |
| 100 | 1.00 | 16.0 | 5 ± 2 |
| 110 | 1.10 | 16.0 | 5 ± 2 |
| 120 | 1.20 | 16.0 | 5 ± 2 |
| 130 | 1.30 | 16.0 | 5 ± 2 |
| 140 | 1.40 | 16.0 | 5 ± 2 |

The instruments are resistant to breakage because the single flute and the wide land provide a web 28 which has a much greater cross-section than in previously available instruments. Thus, the endodontist has better control over the slower rotating instrument 10 that over the previously known faster rotating instruments.

Now with reference to FIGS. 4, 5 and 6 of the drawings, there is shown a remover instrument, generally denoted as the numeral 110, of the present invention for removing gutta percha from a previously obturated tooth. The remover instrument 110 has a shank 112 with a working portion 114. The working portion 114 is tapered along at least a portion of its length toward a tip end 116. The shank 112 above the working portion 114 is illustrated as being substantially cylindrical and is provided with a fitting 118 which is adapted to mate with a chuck of a dental hand piece (not shown).

A single continuous helical flute 120 is formed in the tapered working portion 114 of the shank 112 defining a helical shoulder 122. The shoulder 122 is generally directed upwardly away from the centerline of the shank 112 and away from the tip end 116 of the shank 112. As illustrated, the helical flute 120 follows a right-handed twist so that when it is rotated in a left-handed direction, the shoulder 122 forces the gutta percha material outwardly in a generally radial direction of the working portion 114 from the centerline of the remover instrument 110 and upwardly away from the tip end 116 of the remover instrument 110. However, it is contemplated that the flute 120 can follow a left-handed twist if the instrument 10 is to be operated by a hand piece which rotates in the opposite direction.

In order to minimize abrasion with the walls of the root canal cavity as well as generate sufficient friction to fluidize or plasticize the gutta percha, the periphery of the outer diameter of the shoulder 122 of the flute 120 is provided with a flat surface or peripheral land 124. The land 124 provides a spiraled or helical flat surface at the periphery of the working portion 114 rather than a sharp edge which may contact the walls of the tooth root canal cavity and would also chop up the gutta pecha as the remover instrument 110 is rotated. As shown, the diameter of the land 124 may be progressively reduced as best shown in FIGURE 4 to provide the tapered working portion 114.

As can be best seen in 4 and 6, the flute wall 126 of the flute 120 tapers inwardly from the bottom end of the land 124 toward the inside diameter of the next adjacent succeeding shoulder 122 in a direction toward the tip end 116. The pitch of the flute 120, denoted by the letter "P", remains constant over the length of the working portion 114. The width of the peripheral land, measured along the longitudinal axis of the working portion 114 is at least 40 percent of the flute pitch "P". Preferably, the width of the land 124 is 50 percent of the flute pitch "P". In addition, the width of the land 124 remains constant over the length of the working portion 114.

The helical shoulder 122 is of a constant depth along the entire length of the working portion 114 of the shank 112 and forms a web 128 which has a continuous radial web clearance 130 from the periphery of the working portion 114 as can be best seen in FIG. 5. In transverse cross-section of the shank 112, the peripheral side of the web 128 providing the land 124 measures at least 40 percent of the circumference of the working portion 114 of the shank 112. The helical shoulder 122 is generally cupped or concave, and the leading edge 132 of the shoulder 122 intersects the land 124 at the periphery of the working portion 114 at an included angle "A" of the greater than 90 degrees, thus providing a negative, rake angle flute. In addition, the concave shoulder 122 is asymmetrical with respect to the centerline 134 of the shank 112 such that the apex of the concavity of the shoulder 122 is offset from the shank centerline 34 toward the intersection of the shoulder 122 and land 124, that is toward the leading edge 132 of the shoulder 122. This configuration functions to efficiently move the plasticized gutta percha in an upward direction away from the tip end 116.

To remove gutta percha from a previously obturated tooth root canal, a remover instrument 110 of a size to conform with the size of the root canal cavity is selected and coupled to the chuck of a low speed dental hand piece. The working portion 114 of the shank 112 is inserted into the root canal into contact with the gutta percha to be removed. The rotation of the instrument 110 causes the helical flute 120, shoulder 122, and land to generate frictional heat which plasticizes the gutta percha and mechanically works the plasticized gutta percha generally radially of the shank 112 and upwardly away from the tip end 116 of the shank 112 along the flute 120.

The foregoing detailed description is given primarily for clearness of understanding and no unnecessary limitations are to be understood therefrom for modifications will become obvious to those skilled in the art upon reading this disclosure and may be made without departing from the spirit of the invention and scope of the appended claims.

What is claimed is:

1. An instrument for use with a dental hand piece for thermomechanically obturating a root canal with a thermoplastic material by a process wherein the thermoplastic material is softened by the friction executed by the rotation of the instrument, said instrument comprising an elongated member having a shank at one end thereof which includes a fitting for engagement with a dental hand piece, a tapered working portion at the other end of said member, the diameter of said working portion progressively decreasing away from said shank portion, flute means on said working portion defining a spiral flute having a shoulder facing away from said shank and making an angle with the longitudinal axis of the working portion of greater than 90 degrees to provide a negative rake angle as said instrument is rotated to advance thermoplastic material towards the end of said working portion remote from said shank and a peripheral land adjacent said shoulder having a width which is at least about 40 percent of the pitch of said spiral flute.

2. The instrument of claim 1 wherein the width of said peripheral land is about 50 percent of the pitch of said spiral flute.

3. The instrument of claims 1 or 2 wherein the number of shoulders appearing on a side of the working portion of said instrument over a 16 mm length vary from about 12 for a size 25 instrument to about 5 for a size 140 instrument.

4. An instrument for use with a dental hand piece for thermomechanically removing thermoplastic material from an obturated root canal by a process wherein the thermoplastic material is softened by the friction executed by the rotation of the instrument, said instrument comprising an elongated member having a shank at one end thereof which includes a fitting for engagement with a dental hand piece, a tapered working portion at the other end of said member, the diameter of said working portion progressively decreasing away from said shank portion, flute means on said working portion defining a spiral flute having a shoulder facing away from said shank and making an angle with the longitudinal axis of the working portion of less than 90 degrees to provide a negative rake angle as said instrument is rotated to advance thermoplastic material along said working portion toward said shank and a peripheral land adjacent said shoulder having a width which is at least about 40 percent of the pitch of said spiral flute.

5. The instrument of claim 4 wherein the width of said peripheral land is about 50 percent of the pitch of said spiral flute.

6. The instrument of claims 4 or 5 wherein the number of shoulders appearing on a side of the working portion of said instrument over a 16 mm length vary from about 12 for a size 25 instrument to about 5 for a size 140 instrument.

* * * * *

UNITED STATES PATENT AND TRADEMARK OFFICE
CERTIFICATE OF CORRECTION

PATENT NO. : 4,904,185

DATED : February 27, 1990

INVENTOR(S) : John T. McSpadden

It is certified that error appears in the above-identified patent and that said Letters Patent is hereby corrected as shown below:

Patent Filing Date is in error. It should be November 4, 1988.

Column 1, line 11, "forma" should be -- from a --.

Column 2, line 49, "WIth" should be -- with --.

Column 3, line 67, after "instrument" insert -- 10 --.

Column 4, line 8, "that" should be -- than --.

Column 4, line 41, "that" should be -- than --

Signed and Sealed this

Nineteenth Day of February, 1991

Attest:

HARRY F. MANBECK, JR.

*Attesting Officer*   *Commissioner of Patents and Trademarks*